(12) United States Patent
Sabelle et al.

(10) Patent No.: US 7,241,317 B2
(45) Date of Patent: Jul. 10, 2007

(54) COMPOSITION FOR DYEING KERATIN FIBERS COMPRISING AT LEAST ONE PARA-PHENYLENEDIAMINE SUBSTITUTED WITH A DIAZACYCLOHEPTANE RADICAL

(75) Inventors: Stéphane Sabelle, Paris (FR); Eric Terranova, Magagnose (FR)

(73) Assignee: L'Oreal, S.A., Paris (FR)

( * ) Notice: Subject to any disclaimer, the term of this patent is extended or adjusted under 35 U.S.C. 154(b) by 301 days.

(21) Appl. No.: 10/485,855

(22) PCT Filed: Aug. 7, 2002

(86) PCT No.: PCT/FR02/02822

§ 371 (c)(1),
(2), (4) Date: Sep. 30, 2004

(87) PCT Pub. No.: WO03/014093

PCT Pub. Date: Feb. 20, 2003

(65) Prior Publication Data

US 2005/0102769 A1 May 19, 2005

(30) Foreign Application Priority Data

Aug. 8, 2001 (FR) .................................. 01 10597

(51) Int. Cl.
*A61K 7/13* (2006.01)
(52) U.S. Cl. .................. 8/405; 8/406; 8/410; 8/411; 8/421; 540/575
(58) Field of Classification Search ............... 8/405, 8/406, 410, 411, 421; 540/575
See application file for complete search history.

(56) References Cited

U.S. PATENT DOCUMENTS

| | | |
|---|---|---|
| 4,003,699 A | 1/1977 | Rose et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,766,576 A | 6/1998 | Lowe et al. |
| 6,099,592 A | 8/2000 | Vidal et al. |
| 6,099,593 A | 8/2000 | Terranova et al. |
| 6,165,230 A | 12/2000 | Rose et al. |

FOREIGN PATENT DOCUMENTS

| | | |
|---|---|---|
| DE | 2 359 399 | 6/1975 |
| DE | 3 843 892 A1 | 6/1990 |
| DE | 4 133 957 A1 | 4/1993 |
| DE | 4 241 532 A1 | 6/1994 |
| DE | 195 43 988 A1 | 5/1997 |
| EP | 0 770 375 B1 | 5/1997 |
| EP | 0 962 452 | 12/1999 |
| FR | 2 586 913 A1 | 3/1987 |
| FR | 2 733 749 A1 | 11/1996 |
| FR | 2 750 048 A1 | 12/1997 |
| GB | 1 026 978 | 4/1966 |
| GB | 1 153 196 | 5/1969 |
| JP | 88-169 571 A | 1/1990 |
| JP | 05-163 124 A | 6/1993 |
| JP | 11-139969 | 5/1999 |
| WO | WO 94/08969 A1 | 4/1994 |
| WO | WO 94/08970 A1 | 4/1994 |
| WO | WO 96/15765 A1 | 5/1996 |
| WO | WO 98/38175 | 9/1998 |
| WO | WO 98/58926 | * 12/1998 |
| WO | WO 02/06278 | 1/2002 |

OTHER PUBLICATIONS

STIC Search Report dated Sep. 28, 2006.*
English language Derwent Abstract of JP 11-139969, May 25, 1999.
English language Derwent Abstract of DE 4 241 532, Jun. 16, 1994.
English language Derwent Abstract of EP 0 770 375, May 2, 1997.
English language Derwent Abstract of JP 88-169 571 A, Jan. 23, 1990.
English language Derwent Abstract of JP 05-163 124 A, Jun. 29, 1993.

* cited by examiner

*Primary Examiner*—Eisa Elhilo
(74) *Attorney, Agent, or Firm*—Finnegan, Henderson, Farabow, Garrett & Dunner LLP

(57) ABSTRACT

The subject of the invention is a composition for the oxidation dyeing of keratinous fibers, in particular human hair, comprising an oxidation base of the para-phenylenediamine type, substituted with a diazacycloheptane radical.

The invention also relates to the method for dyeing fibers using this composition, and the novel compounds of the type mentioned above.

25 Claims, No Drawings

COMPOSITION FOR DYEING KERATIN FIBERS COMPRISING AT LEAST ONE PARA-PHENYLENEDIAMINE SUBSTITUTED WITH A DIAZACYCLOHEPTANE RADICAL

The subject of the invention is a composition for the oxidation dyeing of keratinous fibres, in particular human hair, comprising an oxidation base of the para-phenylenediamine type, substituted with a diazacycloheptane radical. The invention also relates to the method for dyeing fibres using this composition, and the novel compounds of the type mentioned above.

It is known to dye keratinous fibres, and in particular human hair, with dyeing compositions containing oxidation dye precursors, generally called oxidation bases, such as ortho- or para-phenylenediamines, ortho- or para-aminophenols and heterocyclic compounds. These oxidation bases are colourless or weakly coloured compounds which, combined with oxidizing products, can give rise, by a process of oxidative condensation, to coloured compounds.

It is also known that the shades obtained with these oxidation bases can be varied by combining them with colour modifiers, generally called couplers, the latter being chosen in particular from aromatic meta-diamines, meta-aminophenols, meta-diphenols and certain heterocyclic compounds such as indole compounds.

The variety of the molecules used in oxidation bases and couplers makes it possible to obtain a rich palette of colours.

The so-called "permanent" colour obtained using these oxidation dyes must moreover meet a number of requirements. Thus, it must be without drawbacks from the toxicological point of view, it must make it possible to obtain shades in the desired intensity and exhibit good resistance to external agents such as light, adverse weather conditions, washing, permanent waving, perspiration and rubbing.

The dyes must also make it possible to cover grey hair, and be the least selective possible, that is to say make it possible to obtain the smallest possible differences in colour right along the same keratinous fibre, which may indeed be differently sensitized (i.e. damaged) between its tip and its root.

It is already known to use 1,4-diazacycloheptane derivatives for the oxidation dyeing of keratinous fibres. For example, Patent U.S. Pat. No. 6,165,230 describes a dyeing composition containing 1,4-diazacycloheptane derivatives substituted on both nitrogen atoms of the ring by an aminobenzene group which makes it possible to obtain intense colorations.

The aim of the present invention is to provide novel compositions for dyeing keratinous fibres, which do not exhibit the disadvantages of those of the prior art. In particular, the aim of the present invention is to provide compositions which contain dyes which are intense, not very selective and particularly resistant, while being capable of generating intense colorations in varied shades, in particular in the basic shades.

This aim is achieved with the present invention whose subject is a composition for the oxidation dyeing of keratinous fibres comprising an oxidation base of the following formula (I) and/or the corresponding addition salts:

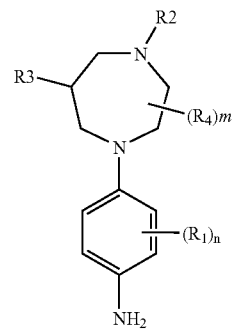

in which:
$R_1$ represents
a halogen atom, preferably chlorine or bromine;
a linear or branched $C_1$-$C_6$ hydrocarbon chain, which is saturated or which may contain one or more double bonds and/or one or more triple bonds, which may form a 3- to 6-membered ring, it being possible for one or more carbon atoms to be replaced by an oxygen, nitrogen or sulphur atom, by an $SO_2$ group, or, when the carbon is terminal, by a halogen atom, preferably a chlorine or bromine atom; the said radical $R_1$ not containing a peroxide bond, or a diazo, nitro or nitroso radical;
n is between 0 and 4 inclusive, it being understood that when n is greater than or equal to 2, then the radicals $R_1$ may be identical or different,
$R_2$ represents
a hydrogen atom;
an alkyl radical which may be unsaturated, unsubstituted or substituted with one or more carboxyl radicals, alkylcarbonyl radicals, alkoxycarbonyl radicals, carbamoyl radicals, mono- or dialkylcarbamoyl radicals, saturated and/or unsaturated, nitrogen-oxygen- and/or sulphur-containing heterocyclic radicals containing 4, 5, 6 or 7 atoms;
an alkyl radical which may be unsaturated, substituted at the 2-position or more by one or more hydroxyl radicals, alkoxy radicals, amino radicals, mono- or dialkylamino radicals, thiol radicals or halogen atoms;
an alkylcarbonyl radical;
an alkoxycarbonyl radical;
a mono- or dialkylcarbamoyl radical;
a carbamoyl radical;
a radical $R_6R_7N\text{—}C\text{=}NR_5\text{—}$ where $R_5$, $R_6$, and $R_7$ represent hydrogen, a $C_1$-$C_4$ alkyl radical or a hydroxyalkyl radical, preferably $R_5$ is hydrogen and $R_6$ and $R_7$ are chosen from hydrogen or a methyl,
$R_3$ represents
a hydrogen atom,
an alkyl radical which may be unsaturated;
a hydroxyl radical;
a hydroxyalkyl radical;
an alkoxy radical;
an alkoxyalkyl radical;
an alkylcarbonyl radical;
a hydroxyalkoxyalkyl radical;
an amino radical;
a monoalkylamino or dialkylamino radical;

an aminoalkyl radical, it being possible for the amine to be mono- or disubstituted with an alkyl, acetyl or hydroxyalkyl radical;
a hydroxy- or aminoalkyl radical;
a carboxyl radical;
a carboxyalkyl radical;
a carbamoyl radical;
a carbamoylalkyl radical;
an alkoxycarbonyl radical;
a mono- or dialkylaminocarbonyl radical;
$R_4$ represents
an alkyl radical which may be unsaturated;
a hydroxyalkyl radical;
an alkoxyalkyl radical;
an alkylcarbonyl radical;
a hydroxyalkoxyalkyl radical;
an aminoalkyl radical, it being possible for the amine to be mono- or disubstituted with an alkyl, acetyl or hydroxyalkyl radical;
a hydroxy- and aminoalkyl radical;
a carboxyl radical;
a carboxyalkyl radical;
a carbamoyl radical;
a carbamoylalkyl radical;
an alkoxycarbonyl radical;
a mono- or dialkylaminocarbonyl radical;
m is between 0 and 4 inclusive, it being understood that when m is greater than or equal to 2, then the radicals $R_4$ may be identical or different.

The compounds of formula (I) are para-phenylenediamines substituted with a substituent of the 1,4-diazacycloheptane type, a substituent also called in the literature 1,4-diazepan.

In the above definitions, the alkyl radicals or groups are linear or branched and comprise, unless otherwise stated, from 1 to 10 carbon atoms, preferably 1 to 6 carbon atoms. An alkoxy radical is an alkyl-O radical, the alkyl group being as defined above.

The expression unsaturated alkyl radical is understood to mean an alkyl of 2 to 10 carbon atoms and comprising one or more double and/or triple bonds.

A substituted alkyl radical is a mono- or polysubstituted alkyl. For example, a hydroxyalkyl or an aminoalkyl is an alkyl which may be substituted with one or more hydroxyl or amino groups. An alkyl radical substituted at the 2-position or more is an alkyl of formula —$CH_2$—R, R being a substituted alkyl.

According to the invention, when it is indicated that one or more of the carbon atoms of the radical $R_1$ may be replaced by an oxygen, nitrogen or sulphur atom or by an $SO_2$ group, and/or that the said radical $R_1$ may contain one or more double bonds and/or one or more triple bonds, that means that it is possible, by way of example, to carry out the following conversions:

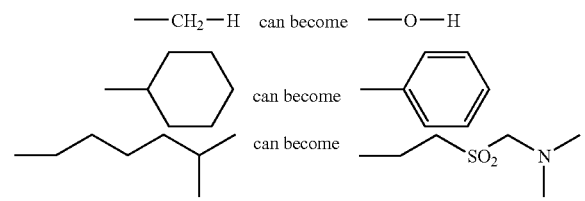

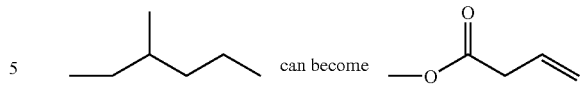

When n is equal to 0, the benzene ring is $NH_2$—$C_6H_4$—N—.

In formula (I), when n is different from zero, the radical $R_1$ is for example chosen from a chlorine atom, or a methyl, ethyl, isopropyl, vinyl, allyl, methoxymethyl, hydroxymethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 1-amino-2-hydroxyethyl, 1,2-diaminoethyl, methoxy, ethoxy, allyloxy or 2-hydroxyethyloxy radical.

When n is defined from zero, $R_1$ is preferably an alkyl, hydroxyalkyl or aminoalkyl, alkoxy, or hydroxyalkoxy radical. In this case, $R_1$ may be chosen from a methyl, hydroxymethyl, 2-hydroxyethyl, 1,2-dihydroxyethyl, methoxy or 2-hydroxyethoxy radical, and more preferably a methyl radical, a hydroxymethyl radical or a 1,2-dihydroxyethyl radical.

According to a preferred embodiment, the oxidation bases of formula (I) are such that n is equal to 0 or 1.

According to a particular embodiment of the invention, the radical $R_2$ is chosen from hydrogen, an alkyl radical, an alkyl radical substituted with a saturated or unsaturated, nitrogen-, oxygen- and/or sulphur-containing heterocyclic containing 4, 5, 6 or 7 atoms, an alkoxycarbonyl radical, an alkyl radical substituted at the 2-position or more with one or more hydroxyl radicals. In this case, $R_2$ may be chosen from the 2-hydroxyethyl radical, the 3-(1-pyrrolidinyl)-propyl radical, the methyl radical, the acetyl radical, hydrogen, and more preferably the 2-hydroxyethyl radical, the methyl radical or hydrogen.

According to a particular embodiment of the invention, $R_3$ is chosen from hydrogen, an alkyl radical, an alkyl radical substituted with one or more hydroxyl radicals, an alkyl radical substituted with one or more amino radicals, or a carboxyl radical. In this case, $R_3$ may be chosen from hydrogen, the hydroxyl radical, the carboxyl radical, the amino radical, the hydroxymethyl radical, or the aminomethyl radical. Among these substituents $R_3$ more preferably represents a hydrogen atom.

According to a particular embodiment, $R_4$ is chosen from hydrogen, an alkyl radical, an alkyl radical substituted with one or more hydroxyl radicals, an alkyl radical substituted with one or more amino radicals, or a carboxyl radical. $R_4$ preferably represents hydrogen.

The carbon substituted with $R_3$ or with $R_4$ may be of the (R) and/or (S) configuration.

The addition salts corresponding to formula (I) may be addition salts with an acid or addition salts with a base.

Among the oxidation bases of formula (I), the following compounds or their addition salts with an acid or a base may be mentioned:

| Formula | Nomenclature |
|---|---|
| | 4-(4-Methyl-[1,4]diazepan-1-yl)phenylamine |
| | 4-[1,4]Diazepan-1-yl-phenylamine |
| | 4-[4-(3-Pyrrolidin-1-yl-propyl)-[1,4]diazepan-1-yl]phenylamine |
| | 2-[4-(4-Amino-phenyl)-[1,4]-diazepan-1-yl]ethanol |
| | 1-[4-(4-Amino-phenyl)-[1,4]-diazepan-1-yl]ethanone |
| | 4-(4-Amino-phenyl)-[1,4]-diazepane-1-carboxamidine |
| | 4-(4-Aminophenyl)-N,N-dimethyl-[1,4]diazepane-1-carboxamidine |
| | 1-(4-Amino-phenyl)-4-methyl-[1,4]-diazepan-6-ol |

-continued

| Formula | Nomenclature |
|---|---|
| | 1-(4-Aminophenyl)-4-methyl-[1,4]-diazepan-6-ylamine |
| | 1-(4-Aminophenyl-4-(3-pyrrolidin-1-yl-propyl)-[1,4]diazepan-6-ol |
| | 1-(4-Aminophenyl)-4-(3-pyrrolidin-1-yl-propyl)-[1,4]diazepan-6-ylamine |
| | 1-(4-Aminophenyl)-4-(2-hydroxyethyl)-[1,4]diazepan-6-ol |

-continued

| Formula | Nomenclature |
|---|---|
| | 2-[6-Amino-4-(4-aminophenyl)-[1,4]diazepan-1-yl]ethanol |
| | 2-[4-(4-Aminophenyl)-6-hydroxymethyl-[1,4]-diazepan-1-yl]ethanol |
| | 2-Methyl-4-(4-methyl-[1,4]-diazepan-1-yl)phenylamine |
| | 4-[1,4]Diazepan-1-yl-2-methyl-phenylamine |

-continued

| Formula | Nomenclature |
|---|---|
| | 2-Methyl-4-[4-(3-pyrrolidin-1-yl-propyl)-[1,4]diazepan-1-yl]phenylamine |
| | 2-[4-(4-Amino-3-methylphenyl)-[1,4]diazepan-1-yl]ethanol |
| | 1-[4-(4-Amino-3-methylphenyl)-[1,4]diazepan-1-yl]ethanone |
| | 4-(4-Amino-3-methylphenyl)-[1,4]-diazepane-1-carboxamidine |

-continued

| Formula | Nomenclature |
|---|---|
| | 4-(4-Amino-3-methylphenyl)-N,N-dimethyl-[1,4]-diazepane-1-carboxamidine |
| | 1-(4-Amino-3-methylphenyl)-4-methyl-[1,4]-diazepan-6-ol |
| | 1-(4-Amino-3-methylphenyl)-4-methyl-[1,4]-diazepan-6-ylamine |
| | 1-(4-Amino-3-methylphenyl)-4-(3-pyrrolidin-1-yl-propyl)-[1,4]-diazepan-6-ol |

-continued

| Formula | Nomenclature |
|---|---|
| | 1-(4-Amino-3-methylphenyl)-4-(3-pyrrolidin-1-yl-propyl)-[1,4]-diazepan-6-ylamine |
| | 1-(4-Amino-3-methylphenyl)-4-(2-hydroxyethyl)-[1,4]-diazepan-6-ol |
| | 2-[6-Amino-4-(4-amino-3-methyl-phenyl)-[1,4]-diazepan-1-yl]ethanol |
| | 2-[4-(4-Amino-3-methylphenyl)-6-hydroxymethyl-1,4]diazepan-1-yl]ethanol |

Preferably, the oxidation bases of formula (I) are chosen from the following compounds and their addition salts with an acid or a base 4-(4-Methyl-[1,4]diazepan-1-yl)phenylamine
4-[1,4]Diazepan-1-yl-phenylamine
4-[4-(3-Pyrrolidin-1-yl-propyl)-[1,4]diazepan-1-yl]phenylamine
2-[4-(4-Aminophenyl)-[1,4]diazepan-1-yl]ethanol
4-[1,4]Diazepan-1-yl-2-methylphenylamine
1-[4-(4-Aminophenyl)-[1,4]diazepan-1-yl]ethanone
4-(4-Aminophenyl)-[1,4]diazepane-1-carboxamidine
4-(4-Aminophenyl)-N,N-dimethyl-[1,4]diazepane-1-carboxamidine
1-(4-Aminophenyl)-4-methyl-[1,4]diazepan-6-ol
3-Methyl-4-(4-methyl-[1,4]diazepan-1-yl)phenylamine
2-Methyl-4-[4-(3-pyrrolidin-1-yl-propyl)-[1,4]diazepan-1-yl]phenylamine
2-[4-(4-Amino-3-methylphenyl)-[1,4]diazepan-1-yl]ethanol
1-[4-(4-Amino-3-methylphenyl)-[1,4]diazepan-1-yl]ethanone
4-(4-Amino-3-methylphenyl)-[1,4]diazepan-1-carboxamidine
4-(4-Amino-3-methylphenyl)-N,N-dimethyl-[1,4]diazepane-1-carboxamidine
1-(4-Amino-3-methylphenyl)-4-methyl-[1,4]diazepan-6-ol.

In the composition of the present invention, the oxidation base(s) of formula (I) are generally present in a quantity of between 0.001 and 10% by weight approximately of the total weight of the dyeing composition, and preferably between 0.005 and 6%.

The compounds of the present invention may be obtained by analogy with methods of preparation described in the literature, see in particular patent application DE 4 241 532 (AGFA).

The composition of the present invention may additionally comprise one or more additional oxidation bases. These additional oxidation bases are chosen from the oxidation bases conventionally used in oxidation dyeing, for example para-phenylenediamines, bisphenylalkylenediamines, para-aminophenols, ortho-aminophenols and heterocyclic bases and their addition salts.

Among the para-phenylenediamines, there may be mentioned more particularly, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis (β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienylpara-phenylenediamine, 2-β-hydroxyethylamino-5-aminotoluene, and their addition salts with an acid.

Among the para-phenylenediamines cited above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines, there may be mentioned more particularly, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-amino-phenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among the para-aminophenols, there may be mentioned more particularly, by way of example, para-aminophenol, 4-amino-3-methylphenol, 4-amino-3-fluoro-phenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, there may be mentioned more particularly, by way of example, 2-aminophenol, 2-amino-5-methylphenol, 2-amino-6-methylphenol, 5-acetamido-2-aminophenol and their addition salts with an acid.

Among the heterocyclic bases, there may be mentioned more particularly, by way of example, the pyridine derivatives, the pyrimidine derivatives and the pyrazole derivatives.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or in Japanese Patents JP 88-169,571 and JP 05 163 124, in European Patent EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750,048 and among which there may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)-amino]ethanol, 2-[(7-aminopyrazolo[1,5-a]pyrimidin-3-yl)-(2-hydroxyethyl)amino]ethanol, 5,6-dimethyl-pyrazolo[1,5-a]pyrimidine-3,7-diamine, 2,6-dimethyl-pyrazole[1,5-a]pyrimidine-3,7-diamine, 2,5, N7, N7-tetramethylpyrazolo [1,5-a]pyrimidine-3,7-diamine, 3-amino-5-methyl-7-imidazolylpropylaminopyrazolo-[1,5-a]pyrimidine, their tautomeric forms, when a tautomeric equilibrium exists, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE-195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxy-methylpyrazole, 4,5-diamino-3-hydroxymethyl-1-methyl-pyrazole, 4,5-diamino-3-hydroxymethyl-1-isopropyl-pyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triamino-pyrazole, 3,5-diamino-1-methyl-4-methylaminopyrazole, 3,5-diamino-4-(β-hydroxyethyl) amino-1-methylpyrazole, and their addition salts with an acid.

The additional oxidation bases are generally present in a quantity of between 0.001 to 10% by weight approximately of the total weight of the dyeing composition, and preferably from 0.005 to 6%.

The composition according to the invention may contain one or more conventional couplers used for dyeing keratinous fibres. Among these couplers, there may be mentioned in particular meta-phenylenediamines, meta-aminophenols, meta-diphenols, naphthalene couplers and heterocyclic couplers and their addition salts.

By way of example, there may be mentioned 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydoxypyridine, 6-hydroxybenzomorpholine, 3,5-diamino-2,6-dimethoxypyridine, 1N-(β-hydroxyethyl)amino-3,4-methylenedioxybenzene, 2,6-bis(β-hydroxyethylamino)toluene, and their addition salts with an acid.

In the composition of the present invention, the coupler(s) are generally present in a quantity of between 0.001 and 10% by weight approximately of the total weight of the dyeing composition, and preferably from 0.005 to 6%.

In general, the addition salts with an acid which can be used in the context of the dyeing compositions of the invention for the oxidation bases of formula (I), the additional oxidation bases and the couplers are chosen in particular from hydrochlorides, hydrobromides, sulphates, citrates, succinates, tartrates, lactates, tosylates, benzenesulphonates, phosphates and acetates.

The addition salts with a base which can be used in the context of the invention are chosen for example from the addition salts with sodium hydroxide, potassium hydroxide, ammonium hydroxide, amines and alkanolamines.

The dyeing composition in accordance with the invention may additionally contain one or more direct dyes which may be chosen in particular from nitro dyes of the benzene series, cationic direct dyes, azo direct dyes, methene direct dyes.

The medium appropriate for dyeing also called dye carrier generally consists of water or of a mixture of water and of at least one organic solvent to solubilize the compounds which might not be sufficiently soluble in water. As organic solvent, there may be mentioned for example lower $C_1$-$C_4$ alkanols, such as ethanol and isopropanol; polyols or polyol ethers such as 2-butoxyethanol, propylene glycol, monomethyl ether of propylene glycol, monoethyl ether and monomethyl ether of diethylene glycol, as well as aromatic alcohols such as benzyl alcohol or phenoxyethanol, and mixtures thereof.

The solvents may be present in proportions preferably of between 1 and 40% by weight approximately relative to the total weight of the dyeing composition, and still more preferably between 5 and 30% by weight approximately.

The dyeing composition in accordance with the invention may also contain various adjuvants which are conventionally used in hair-dyeing compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, and in particular anionic, cationic, nonionic and amphoteric polymeric associative thickeners, antioxidants, penetrating agents, sequestering agents, perfumes, buffers, dispersing agents, conditioning agents such as for example modified or unmodified, volatile or nonvolatile silicones, film-forming agents, ceramides, preservatives and opacifying agents.

These above adjuvants are generally present in a quantity for each of them of between 0.01 and 20% by weight relative to the weight of the composition.

Of course, persons skilled in the art will be careful to choose this or these possible additional compounds such that the advantageous properties intrinsically attached to the oxidation dyeing composition in accordance with the invention are not, or not substantially, impaired by the addition(s) envisaged.

The pH of the dyeing composition in accordance with the invention is generally between 3 and 12 approximately, and preferably between 5 and 11 approximately. It can be adjusted to the desired value by means of acidifying or alkalinizing agents normally used in dyeing keratinous fibres or using conventional buffer systems.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and triethanolamines as well as derivatives thereof, sodium or potassium hydroxides and the compounds of the following formula (III):

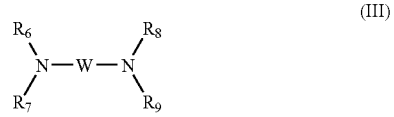

(III)

in which W is a propylene residue optionally substituted by a hydroxyl group or a $C_1$-$C_4$ alkyl radical; $R_6$, $R_7$, $R_8$ and $R_9$, which are identical or different, represent a hydrogen atom, a $C_1$-$C_4$ alkyl or $C_1$-$C_4$ hydroxyalkyl radical.

The dyeing composition according to the invention may be provided in various forms, such as in the form of liquids, creams, gels or in any other form appropriate for carrying out a dyeing of keratinous fibres, and in particular human hair.

The subject of the invention is also a method of dyeing keratinous fibres, and in particular human keratinous fibres such as hair, using the dyeing composition as defined above.

According to this method, the composition according to the present invention is applied to the fibres, the colour being developed with the aid of an oxidizing agent. The colour may be developed at an acidic, neutral or alkaline pH and the oxidizing agent may be added to the composition of the invention just at the time of use or it may be used from an oxidizing composition containing it, applied simultaneously or sequentially to the composition of the invention.

According to a particular embodiment, the composition according to the present invention is mixed, preferably at the time of use, with a composition containing, in a medium appropriate for dyeing, at least one oxidizing agent, this oxidizing agent being present in a sufficient quantity to develop a colour. The mixture obtained is then applied to the keratinous fibres. After an exposure time of 3 to 50 minutes approximately, preferably 5 to 30 minutes approximately, the keratinous fibres are rinsed, washed with shampoo, rinsed again and then dried.

The oxidizing agents conventionally used for the oxidation dyeing of keratinous fibres are for example hydrogen peroxide, urea peroxide, alkali metal bromates, persalts such as perborates and persulphates, peracids and oxidase enzymes among which there may be mentioned peroxidases, oxidoreductases containing two electrons such as uricases and oxygenases containing 4 electrons such as laccases. Hydrogen peroxide is particularly preferred.

The oxidizing composition may also contain various adjuvants conventionally used in hair dyeing compositions and as defined above for the composition of the invention.

The pH of the oxidizing composition containing the oxidizing agent is such that after mixing with the dyeing composition, the pH of the resulting composition applied to the keratinous fibres varies between 3 and 12 approximately, and preferably between 5 and 11. It can be adjusted to the desired value by means of acidifying or alkalinizing agents normally used for dyeing keratinous fibres and as defined above.

The composition which is finally applied to the keratinous fibres may be provided in various forms, such as in the form of liquids, creams, gels, or in any other form appropriate for dyeing keratinous fibres, and in particular human hair.

Another subject of the invention is a multicompartment device or dyeing "kit" in which a first compartment contains the dyeing composition defined above and a second compartment contains the oxidizing composition. This device may be equipped with a means which makes it possible to deliver the desired mixture onto the hair, such as the devices described in patent FR-2 586 913 in the name of the applicant.

Finally, the subject of the invention is also the coloured product which can be obtained by oxidative condensation of the composition of the present invention. This composition comprises at least one oxidation base of formula (I) as defined above in the presence of at least one oxidizing agent as defined above and optionally in the presence of at least one coupler and/or at least one additional oxidation base.

These coloured products may be provided in particular in the form of pigments and may be used as direct dyes for the direct dyeing of hair or may be incorporated into cosmetic products such as for example into makeup products.

The subject of the present invention is finally the novel para-phenylenediamine derivatives of formula (I) with the exception of 4-(4-methyl-[1,4]diazepan-1-yl)phenylamine.

The examples which follow serve to illustrate the invention without however exhibiting a limiting character.

EXAMPLES

Example 1

Synthesis of 4-(4-methyl-[1,4]diazepan-1-yl)phenylamine dihydrochloride (2)

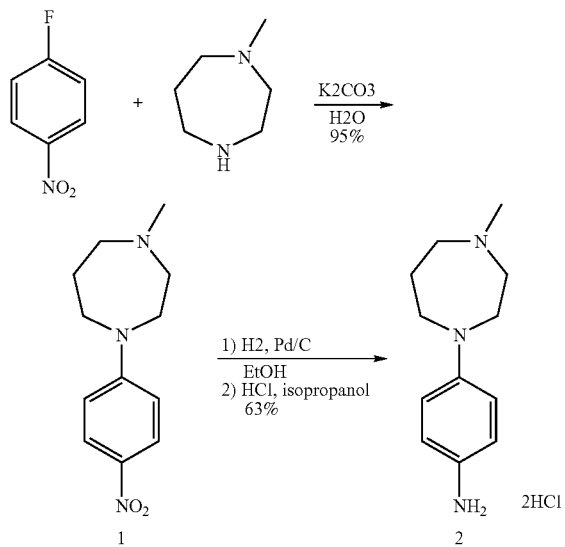

Step 1: Synthesis of 1-methyl-4-(4-nitrophenyl)-[1,4]diazepane (1)

Fluoronitrobenzene (10.3 g, 0.073 mol) is dissolved in water and then potassium carbonate (12.1 g, 0.0876 mol) is added. 1-Methyl[1,4]diazepane (10 g, 0.0876 mol) is introduced and then the reaction medium is heated under reflux (≅100° C.) for 5 hours. The medium is cooled. A precipitate forms, which is filtered and washed with water. A yellow solid is recovered, which is dried at 45° C. in a vacuum oven (16.21 g, yield=94.5%).

Spectroscopic Data:
$^1$H NMR (DMSO d6, 200 MHz): 1.63-1.75 (m, 2H), 2.06 (s, 3H), 2.22-2.33 (m, 2H), 2.40-2.45 (m, 2H), 3.34-3.51 (m, 4H), 6.58-6.66 (m, 2H), 7.79-7.88 (m, 2H)

Step 2: Synthesis of 4-(4-methyl-[1,4]diazepan-1-yl)phenylamine, dihydrochloride (2)

In a stainless steel hydrogenating reactor, 6 g of 1-methyl-4-(4-nitrophenyl)-[1,4]diazepane (1) (25.5 mmol) are partially dissolved in 300 ml of ethanol. 2.1 g of 5% Pd/C (50% moist) are added, the reactor is closed and purged with nitrogen 3 times, with stirring (1800 rpm). Hydrogen is then introduced at a pressure of 12 bar at room temperature for 4 hours. The reactor is then purged with nitrogen and the reaction medium is filtered under a nitrogen atmosphere and the filtrate is immediately recovered in a solution containing 9.6 ml of 37% hydrochloric acid and 50 ml of isopropanol. The filtrate is then concentrated until a precipitate is obtained. The solid is filtered, washed with isopropanol and then dried under vacuum in the presence of potassium hydroxide. 4.5 g (63%) of 4-(4-methyl-[1,4]diazepan-1-yl) phenylamine, dihydrochloride (2) are thus obtained in the form of a white solid.

Spectroscopic Data:
$^1$H NMR (D20 d6, 400 MHz): 2.16 (m, 1H), 2.35 (m, 1H), 2.77 (s, 3H), 3.08-3.15 (m, 2H), 3.38-3.46 (m, 4H), 3.73-3.80 (m, 2H), 6.82 (d, J=9.2 Hz, 2H), 7.21 (d, J=9.2 Hz, 2H)

$^{13}$C NMR (MeOD, 100 MHz): 23.3, 43.05, 43.44, 46.85, 54.90, 55.88

Mass spectrum: spectrum in conformity with the structure.

Example 2

Synthesis of 4-[1,4]diazepan-1-yl-2-methylphenylamine, dihydrochloride (3)

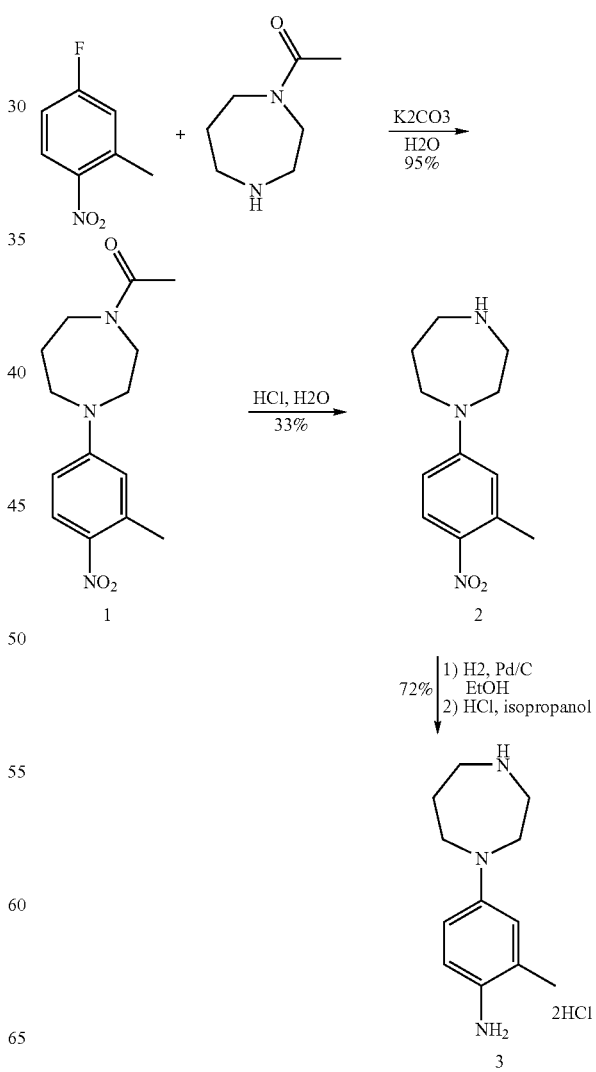

Step 1: Synthesis of 1-(3-methyl-4-nitrophenyl)-[1,4]diazepane (1)

Fluoronitrobenzene (9.1 g, 0.0586 mol) is dissolved in water (50 ml) and then potassium carbonate (9.7 9, 0.0703 mol) and 1-acetyl-[1,4]diazepane (10 g, 0.0703 mol) are added. The medium is heated at 95° C. for 6 hours, and an orange-coloured solution is obtained. The medium is then cooled to room temperature, and an orange-coloured sticky paste then appears. The maximum amount of water is removed from the reaction medium. Isopropanol is then added to the paste until a yellow solid precipitates. The medium is filtered and, after drying in a vacuum oven at 45° C., a yellow powder is obtained which corresponds to 1-(3-methyl-4-nitrophenyl)-[1,4]diazepane (1). (8.7 g; Yield=53.6%)

Spectroscopic Data:
$^1$H NMR (DMSO d6, 200 MHz): 1.57-1.81 (m, 5H), 2.39 (s, 3H), 3.13-3.25 (m, 4H), 3.38-3.52 (m, 5H), 3.60-3.65 (m, 1H), 6.56-6.63 (m, 2H), 7.79-7.85 (m, 1H)

Step 2: Synthesis of 1-(3-methyl-4-nitrophenyl)-[1,4]diazepane (2)

1-(3-Methyl-4-nitrophenyl)-[1,4]diazepane 1 (8 g, 0.0289 mol) is suspended in a 37% HCl solution (29 ml) in water (145 ml). The medium is heated under reflux (100° C.) for 30 hours. It is allowed to cool, and a brown precipitate is then obtained. About 30 ml of 35% sodium hydroxide are added to pH=7. The reaction medium is then concentrated until a solid appears. After filtration, this solid is recrystallized from an isopropanol/methanol mixture. A brown powder is thus obtained which corresponds to 1-(3-methyl-4-nitrophenyl)-[1,4]diazepane (2). (2.4 g, Yield=33%)

Spectroscopic Data:
$^1$H NMR (DMSO d6, 200 MHz): 2.18 (m, 2H), 2.65 (s, 3H), 3.12-3.14 (m, 2H), 3.25 (m, 2H), 3.70-3.76 (m, 2H), 3.92 (m, 2H), 6.84 (m, 2H), 8.02-8.12 (m, 1H), 9.03-9.33 (m, 1H)

Step 3: Synthesis of 4-[1,4]diazepan-1-yl-2-methylphenylamine, dihydrochloride (3)

In a stainless steel hydrogenating reactor, 2.34 g of 1-(3-methyl-4-nitrophenyl)-[1,4]diazepane 2 (9.96 mmol) are dissolved in 150 ml of ethanol. 1.2 g of 5% Pd/C (50% moist) are added, the reactor is closed and purged with nitrogen 3 times, with stirring (1800 rpm). Hydrogen is then introduced at a pressure of 9 bar at room temperature for 3 hours. The reactor is then purged with nitrogen and the reaction medium is filtered under a nitrogen atmosphere and the filtrate is immediately recovered in a solution containing 3.7 ml of 37% hydrochloric acid and 16 ml of isopropanol. The filtrate is then concentrated until a precipitate is obtained. The solid is filtered, washed with isopropanol and then dried under vacuum in the presence of potassium hydroxide. 2 g (72%) of 4-[1,4]diazepan-1-yl)-2-methylphenylamine, dihydrochloride (3) are thus obtained in the form of a white solid.

Spectroscopic Data:
$^1$H NMR (D20 d6, 400 MHz): 1.92-1.99 (m, 2H), 2.09 (m, 3H), 3.03-3.09 (m, 2H), 3.18-3.23 (m, 2H), 3.36-3.40 (m, 2H), 3.56-3.61 (m, 2H), 6.59-6.60 (m, 2H), 7.00 (d, J=8.7 Hz, 1H)

Mass spectrum: spectrum in conformity

Example 3

Synthesis of 4-[4-(3-pyrrolidin-1-yl-propyl)-[1,4] diazepan-1-yl)phenylamine, trihydrochloride (2)

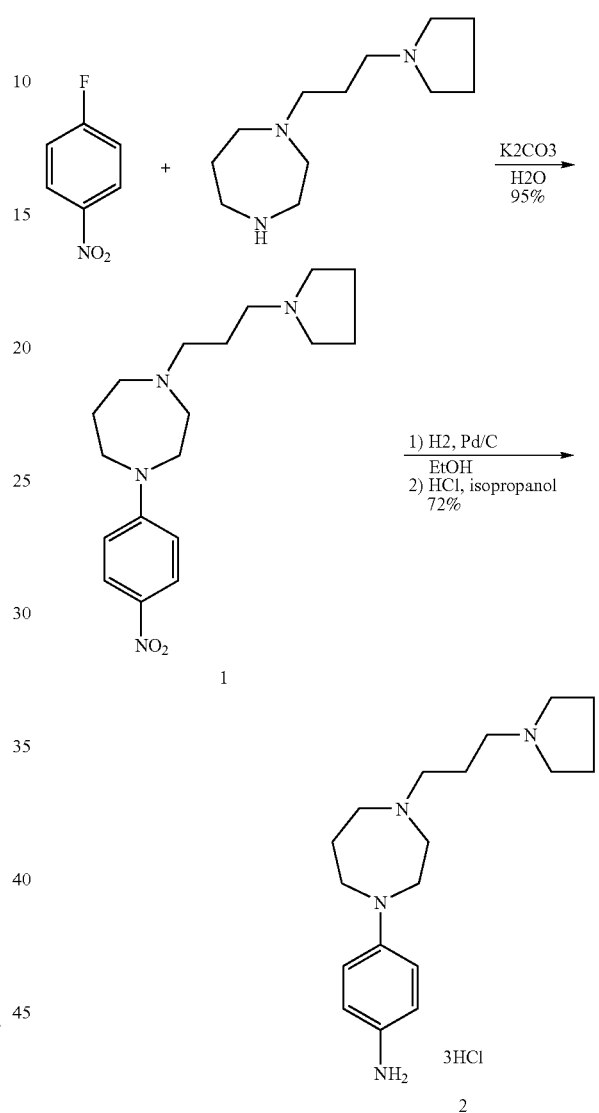

Step 1: Synthesis of 1-(4-nitrophenyl)-4-(3-pyrrolidin-1-yl-propyl)-[1,4]diazepane (1)

Fluoronitrobenzene (5.56 g, 39.43 mmol) is dissolved in water, and then potassium carbonate (6.55 g, 47.31 mmol) and 1-(3-pyrrolidinopropyl)-homopiperazine (10 g, 47.31 mmol) are added. The medium is heated at 85° for 4 hours and then cooled to room temperature. The medium is filtered and a yellow solid is recovered after drying in a vacuum oven at 45° C. (12.5 g, yield=95.5%).

Spectroscopic Data
$^1$H NMR (DMSO d6, 200 MHz): 1.55-1.71 (m, 6H), 1.90-1.96 (m, 2H), 2.32-2.61 (m, 10H), 2.75-2.80 (m, 2H), 3.63-3.73 (m, 4H), 6.89 (d, J=9.4 Hz, 2H), 8.09 (d, J=9.4 Hz, 2H)

Step 2: Synthesis of 4-[4-(3-pyrrolidin-1-yl-propyl)-[1,4]diazepan-1-yl]phenylamine, trihydrochloride (2)

In a stainless steel hydrogenating reactor, 6.6 g of 1-(4-nitrophenyl)-4-(3-pyrrolidin-1-yl-propyl)-[1,4]diazepane (1) (19.9 mmol) are partially dissolved in 300 ml of ethanol. 2.3 g of 5% Pd/C (50% moist) are added, the reactor is closed and purged with nitrogen 3 times, with stirring (1800 rpm). Hydrogen is then introduced at a pressure of 10 bar at room temperature for 3 hours. The reactor is then purged with nitrogen and the reaction medium is filtered under a nitrogen atmosphere and the filtrate is immediately recovered in a solution containing 9.1 ml of 37% hydrochloric acid and 40 ml of isopropanol. The filtrate is then concentrated until a precipitate is obtained. The solid is filtered, washed with isopropanol and then dried under vacuum in the presence of potassium hydroxide. 5.9 g (72%) of 4-[4-(3-pyrrolidin-1-yl-propyl)-[1,4]diazepan-1-yl)phenylamine trihydrochloride (2) are thus obtained in the form of a white solid.

Spectroscopic Data:

$^1$H NMR (D20 d6, 500 MHz): 2.02-2.04 (m, 2H), 2.18 (m, 2H), 2.18-2.31 (m, 4H), 3.12-3.14 (m, 2H), 3.30-3.35 (m, 4H), 3.57-3.59 (m, 2H), 3.71-3.72 (m, 2H), 3.87 (m, 2H), 6.94 (d, J=8.9 Hz, 2H), 7.32 (d, J=8.9 Hz, 2H)

Mass spectrum: spectrum in conformity with the structure.

Example 4

Synthesis of 4-[1,4]diazepan-1-yl-phenylamine, dichlorohydrate (2)

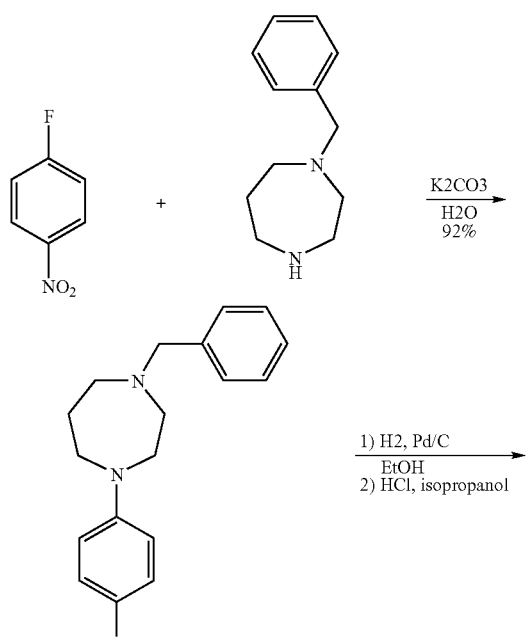

Step 1: Synthesis of 1-benzyl-4-(4-nitrophenyl)-[1,4]diazepane (1)

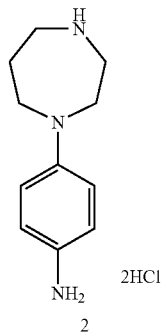

Fluoronitrobenzene (3.09 g, 21.9 mmol) is dissolved in water (14 ml), and then potassium carbonate (3.64 g, 26.28 mmol) and 1-benzylhomopiperazine (5 g, 26.28 mmol) are added. The medium is heated at 90° C. for 4 h 20 min and then cooled to room temperature. The precipitate formed is filtered, and a yellow solid is obtained. 6.30 g (92.5%) of product are recovered.

Spectroscopic Data $^1$H NMR (DMSO d6, 500 MHz): 2.08-2.16 (m, 2H), 2.74-2.80 (m, 2H), 2.92-2.97 (m, 2H), 3.85-3.92 (m, 6H), 7.07 (d, J=9.5 Hz, 2H), 7.44-7.59 (m, 5H), 8.27 (d, J=9.5 Hz, 2H)

Step 2: Synthesis of 4-[1,4]diazepan-1-yl-phenylamine, dihydrochloride (2)

In a stainless steel hydrogenating reactor, 6.3 g of 1-benzyl-4-(4-nitrophenyl)-(1,4)diazepane 1 (22.26 mmol) are partially dissolved in 170 ml of ethanol. 2.3 g of 5% Pd/C (50% moist) are added, the reactor is closed and purged with nitrogen 3 times, with stirring (1800 rpm). Hydrogen is then introduced at a pressure of 11 bar, the medium is heated to a temperature of 60° C. and then allowed to cool for 3.5 hours. The reactor is then purged with nitrogen and the reaction medium is filtered under a nitrogen atmosphere and the filtrate is immediately recovered in a solution containing 7.6 ml of 37% hydrochloric acid and 30 ml of isopropanol. The filtrate is then concentrated until a precipitate is obtained. The solid is filtered, washed with isopropanol and then dried under vacuum in the presence of potassium hydroxide. 4.6 g of 4-[1,4]diazepan-1-yl-phenylamine, dihydrochloride (2) are thus obtained in the form of a white solid.

Spectroscopic Data:

$^1$H NMR (D20, 500 MHz): 2.23-2.28 (m, 2H), 3.36-3.39 (m, 2H), 3.52-3.54 (m, 2H), 3.65-3.69 (m, 2H), 3.89-3.91 (m, 2H), 7.07 (m, 2H), 7.37 (m, 2H)

Mass spectrum: spectrum in conformity with the structure.

Example 5

Synthesis of 2-[4-(4-aminophenyl)-[1,4]diazepan-1-yl]ethanol, dihydrochloride (2)

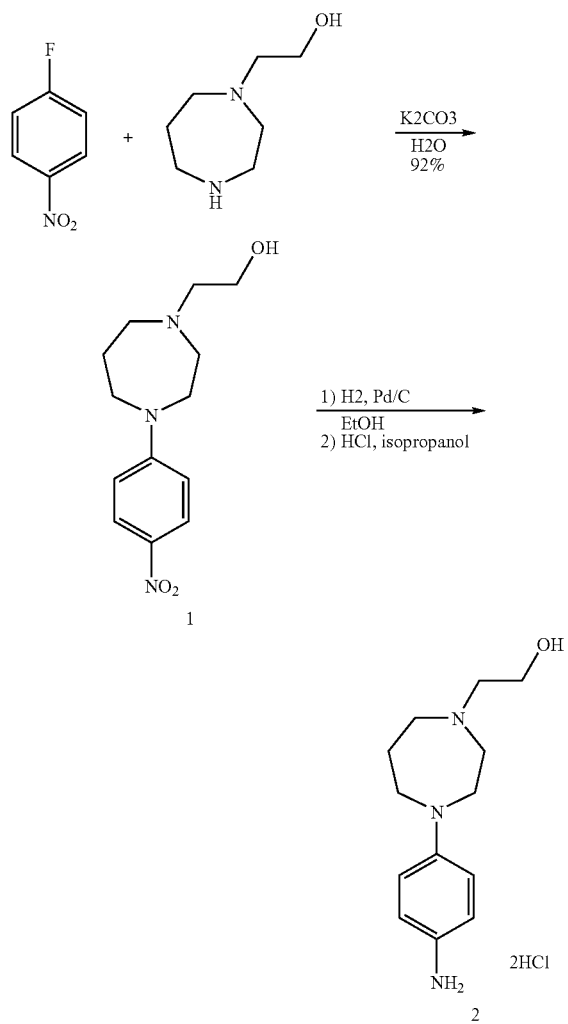

Step 1: Synthesis of 2-[4-(4-nitrophenyl)-[1,4]diazepan-1-yl]ethanol (1)

Fluoronitrobenzene (2.03 g, 14.4 mmol) is dissolved in water (10 ml), and then potassium carbonate (2.4 g, 17.3 mmol) and 1-(2-hydroxyethyl)-homopiperazine are added. The medium is heated at 95° C. for 4 hours and then cooled to room temperature and filtered. A dark orange-coloured powder is recovered which is placed in the oven (3.5 g, yield=91.7%).

Spectroscopic Data $^1$H NMR (DMSO d6, 200 MHz): 1.66-1.78 (m, 2H), 2.37-2.48 (m, 6H), 2.63-2.68 (m, 2H), 3.29-3.35 (m, 2H), 3.44-3.69 (m, 4H), 4.26 (m, 1H), 6.66-6.74 (m, 2H), 7.86-7.95 (m, 2H)

Step 2: Synthesis of 2-[4-(4-aminophenyl)-[1,4]diazepan-1-yl]ethanol, dihydrochloride (2)

In a stainless steel hydrogenating reactor, 6.9 g of 2-[4-(4-nitrophenyl)-[1,4]diazepan-1-yl]ethanol (26.04 mmol) are partially dissolved in 350 ml of ethanol. 2.5 g of 5% Pd/C (50% moist) are added, the reactor is closed and purged with nitrogen 3 times, with stirring (1800 rpm). Hydrogen is then introduced at a pressure of 9 bar for 4.5 hours. The reactor is then purged with nitrogen and the reaction medium is filtered under a nitrogen atmosphere and the filtrate is immediately recovered in a solution containing 9.8 ml of 37% hydrochloric acid and 40 ml of isopropanol. The filtrate is then concentrated until a precipitate is obtained. The solid is filtered, washed with isopropanol and then dried under vacuum in the presence of potassium hydroxide. 7.8 g of 2-[4-(4-aminophenyl)-[1,4]diazepan-1-yl]ethanol, dihydrochloride (2) are thus obtained in the form of a white solid.

Spectroscopic Data:

$^1$H NMR (D20 d6, 500 MHz): 2.17-2.18 (m, 1H), 2.49-2.50 (m, 1H), 3.10-3.21 (m, 4H), 3.41-3.55 (m, 4H), 3.78-3.81 (m, 4H), 6.83 (m, 2H), 7.22 (m, 2H)

Mass spectrum: spectrum in conformity with the structure.

Elemental analysis

|        | % C   | % H  | % N   | % O  | % Cl  |
|--------|-------|------|-------|------|-------|
| Theory | 50.66 | 7.52 | 13.63 | 5.19 | 23    |
| Found  | 50.17 | 7.53 | 13.59 | 5.49 | 22.99 |

EXAMPLES OF COMPOSITIONS

The following compositions were prepared (content of the bases and couplers in mol)

| Examples | 6 | 7 | 8 | 9 | 10 | 11 | 12 |
|---|---|---|---|---|---|---|---|
| 4-[1,4]Diazepan-1-yl-2-methylphenylamine, trihydrochloride | $3 \times 10^{-3}$ | $3 \times 10^{-3}$ | $3 \times 10^{-3}$ | $3 \times 10^{-3}$ | — | — | — |
| 4-[4-(3-Pyrrolidin-1-yl-propyl)-[1,4]diazepan-1-yl]phenylamine, trihydrochloride | — | — | — | — | $3 \times 10^{-3}$ | $3 \times 10^{-3}$ | $3 \times 10^{-3}$ |
| 1,3-Dihydroxybenzene | — | $3 \times 10^{-3}$ | — | — | $3 \times 10^{-3}$ | — | — |
| 1-β-Hydroxyethyloxy-2,4-diaminobenzene, 2HCl | — | — | $3 \times 10^{-3}$ | — | — | $3 \times 10^{-3}$ | — |
| 2-Methyl-5-aminophenol | — | — | — | $3 \times 10^{-3}$ | — | — | $3 \times 10^{-3}$ |

-continued

| Dye carrier | (*) | (*) | (*) | (*) | (*) | (*) | (*) |
|---|---|---|---|---|---|---|---|
| Demineralized water qs | 100 g | 100 g | 100 g | 100 g | 100 g | 100 g | 100 g |
| Examples | 13 | 14 | 15 | 16 | 17 | 18 | 19 | 20 |

| | 13 | 14 | 15 | 16 | 17 | 18 | 19 | 20 |
|---|---|---|---|---|---|---|---|---|
| 4-[1,4]Diazepan-1-yl-phenylamine, dihydrochloride | $3 \times 10^{-3}$ | $3 \times 10^{-3}$ | $3 \times 10^{-3}$ | $3 \times 10^{-3}$ | — | — | — | — |
| 2-[4-(4-Aminophenyl)-[1,4]diazepan-1-yl]ethanol, trihydrochloride | — | — | — | — | $3 \times 10^{-3}$ | $3 \times 10^{-3}$ | $3 \times 10^{-3}$ | $3 \times 10^{-3}$ |
| 1,3-Dihydroxybenzene | — | $3 \times 10^{-3}$ | — | — | — | $3 \times 10^{-3}$ | — | — |
| 1-β-Hydroxyethyloxy-2,4-diaminobenzene, 2HCl | — | — | $3 \times 10^{-3}$ | — | — | — | $3 \times 10^{-3}$ | — |
| 2-Methyl-5-aminophenol | — | — | — | $3 \times 10^{-3}$ | — | — | — | $3 \times 10^{-3}$ |
| Dye carrier | (*) | (*) | (*) | (*) | (*) | (*) | (*) | (*) |
| Demineralized water qs | 100 g | 100 g | 100 g | 100 g | 100 g | 100 g | 100 g | 100 g |

(*) Common dye carrier:

| | |
|---|---|
| Polyglycerolated oleyl alcohol containing 2 mol of glycerol | 4.0 g |
| Polyglycerolated oleyl alcohol containing 4 mol of glycerol, containing 78% of active substances (A.S.) | 5.69 g A.S. |
| Oleic acid | 3.0 g |
| Oleyl amine containing 2 mol of ethylene oxide, sold under the trade name ETHOMEEN O12 by the company AKZO | 7.0 g |
| Diethylaminopropyl laurylamino succinamate, sodium salt containing 55% of A.S. | 3.0 g A.S. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulfite as an aqueous solution containing 35% of A.S. | 0.455 g A.S. |
| Ammonium acetate | 0.8 g |
| Antioxidant, sequestrant | q.s. |
| Perfume, preservative | q.s. |
| Aqueous ammonia containing 20% of $NH_3$ | 10.0 g |

At the time of use, each composition is mixed with an equal weight of hydrogen peroxide at 20 volumes (6% by weight).

Each mixture obtained is applied to locks of natural or permanently waved grey hair which is 90% white. After leaving for 30 min, the locks are rinsed, washed with a standard shampoo, rinsed again and then dried.

The colour of the locks was evaluated in the L*a*b* system by means of a MINOLTA CM 2002 spectrophotometer.

In the L*a*b* space, the clarity is indicated by the value L* on a scale from 0 to 100 whereas the chromatic coordinates are expressed by a* and b* which indicate two colour axes, a* the green-red axis and b* the blue-yellow axis.

According to this system, the higher the value of L, the lighter and less intense the colour. Conversely, the lower the value of L, the darker or more intense the colour.

The results are presented in Table 1 below.

TABLE 1

| Examples | Nature of the locks | L* | a* | b* |
|---|---|---|---|---|
| Ref. 1 | natural | 61.06 | 0.72 | 11.74 |
| Ref. 2 | permanently waved | 59.7 | 0.24 | 9.10 |
| 6 | natural | 50.38 | 3.45 | 7.46 |
| 7 | natural | 38.86 | 5.30 | 5.97 |
| 8 | natural | 28.26 | −0.41 | −12.60 |
| 9 | natural | 32.71 | 10.85 | −7.57 |
| 10 | natural | 32.01 | 5.87 | 3.38 |
| 11 | natural | 27.47 | −0.98 | −11.14 |
| 12 | natural | 33.39 | 8.39 | −7.77 |
| 13 | natural | 55.66 | 4.21 | 10.12 |
| 14 | natural | 49.12 | 3.93 | 9.59 |
| 15 | natural | 39.85 | −5.27 | −0.29 |
| 16 | natural | 45.92 | −0.57 | −3.41 |
| 17 | natural | 39.97 | 1.53 | 5.77 |
| 17 | permanently waved | 33.47 | 2.56 | 5.98 |
| 18 | natural | 30.79 | 5.35 | 4.86 |
| 18 | permanently waved | 25.74 | 4.60 | 3.94 |
| 19 | natural | 22.04 | 2.19 | −10.60 |
| 19 | permanently waved | 20.04 | 1.67 | −5.66 |
| 20 | natural | 25.15 | 9.51 | −5.83 |
| 20 | permanently waved | 20.50 | 6.67 | −4.54 |

The invention claimed is:

1. A composition for the oxidation dyeing of keratin fibers comprising:
   a medium suitable for dyeing, and
   at least one oxidation base comprised in said medium and chosen from compounds of the following formula (I) and the addition salts thereof:

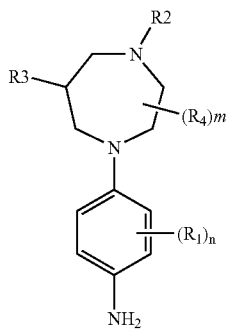

(I)

wherein:
   $R_1$ is chosen from:
      a halogen atom; and
      linear and branched $C_1$-$C_6$ hydrocarbon chains, wherein the hydrocarbon chains may be saturated or may comprise at least one bond chosen from double bonds and triple bonds, the hydrocarbon chains may form at least one ring chosen from 3- to 6-membered rings, wherein at least one carbon atom can be replaced by at least one entity chosen from oxygen, nitrogen and sulphur atoms, and an $SO_2$ group, or, when the carbon is terminal, it may be replaced by a halogen atom; provided that the radical $R_1$ does not comprise a peroxide bond, a diazo radical, a nitro radical, or a nitroso radical;
   n is a number ranging from 0 to 4 inclusive, it being understood that when n is greater than or equal to 2, then the radicals $R_1$ may be identical or different;
   $R_2$ is chosen from:
      a hydrogen atom;
      alkyl radicals which may be unsaturated, unsubstituted and substituted with at least one radical chosen from carboxyl radicals, alkylcarbonyl radicals, alkoxycarbonyl radicals, carbamoyl radicals, mono- and dialkylcarbamoyl radicals, saturated and unsaturated, nitrogen-oxygen- and sulphur-comprising heterocyclic radicals comprising 4, 5, 6 or 7, identical or different, atoms;
      alkyl radicals which may be unsaturated, substituted at least at the 2-position by at least one radical chosen from hydroxyl radicals, alkoxy radicals, amino radicals, mono- and dialkylamino radicals, thiol radicals and halogen atoms;
      an alkylcarbonyl radical;
      an alkoxycarbonyl radical;
      a monoalkylcarbamoyl and dialkylcarbamoyl radical;
      a carbamoyl radical; and
      a radical $R_6R_7N—C=NR_5—$ wherein $R_5$, $R_6$, and $R_7$, which may be identical or different, are each chosen from hydrogen, $C_1$-$C_4$ alkyl radicals and hydroxyalkyl radicals;
   $R_3$ is chosen from:
      a hydrogen atom;
      alkyl radicals which may be unsaturated;
      a hydroxyl radical;
      a hydroxyalkyl radical;
      an alkoxy radical;
      an alkoxyalkyl radical;
      an alkylcarbonyl radical;
      a hydroxyalkoxyalkyl radical;
      an amino radical;
      a monoalkylamino and a dialkylamino radical;
      an aminoalkyl radical, it being possible for the amine to be mono- or disubstituted with at least one identical or different radical chosen from alkyl, acetyl and hydroxyalkyl radicals;
      a hydroxy- and aminoalkyl radical;
      a carboxyl radical;
      a carboxyalkyl radical;
      a carbamoyl radical;
      a carbamoylalkyl radical;
      an alkoxycarbonyl radical; and
      a monoalkylaminocarbonyl and a dialkylaminocarbonyl radical;
   $R_4$ is chosen from:
      alkyl radicals which may be unsaturated;
      a hydroxyalkyl radical;
      an alkoxyalkyl radical;
      an alkylcarbonyl radical;
      a hydroxyalkoxyalkyl radical;
      an aminoalkyl radical, wherein the amine may be mono- or disubstituted with at least one identical or different radical chosen from alkyl, acetyl and hydroxyalkyl radicals;
      a hydroxy- and aminoalkyl radical;
      a carboxyl radical;
      a carboxyalkyl radical;
      a carbamoyl radical;
      a carbamoylalkyl radical;
      an alkoxycarbonyl radical; and
      a monoalkylaminocarbonyl and a dialkylaminocarbonyl radical; and
   m is a number ranging from 0 to 4 inclusive, it being understood that when m is greater than or equal to 2, then the radicals $R_4$ may be identical or different;
   wherein said at least one oxidation base is present in said composition in an amount effective to dye keratin fibers.

2. The composition according to claim 1, wherein, in $R_1$, the halogen atom is chosen from chlorine and bromine.

3. The composition according to claim 1, wherein $R_2$ is radical $R_6R_7N—C=NR_5—$, wherein $R_5$ is a hydrogen atom and $R_6$ and $R_7$, which may be identical or different, are each chosen from a hydrogen atom and a methyl radical.

4. The composition according to claim 1, wherein $R_1$ is chosen from alkyl, hydroxyalkyl, aminoalkyl, alkoxy, and hydroxyalkoxy radicals.

5. The composition according to claim 1, wherein $R_1$ is chosen from methyl, hydroxymethyl, 2-hydroxyethyl, 1,2-dihydroxyethyl, methoxy, and 2-hydroxyethoxy radicals.

6. The composition according to claim 1, wherein n is equal to 0 or 1.

7. The composition according to claim 1, wherein $R_2$ is chosen from hydrogen, alkyl radicals, alkyl radicals substituted with at least one entity chosen from saturated and unsaturated, nitrogen-, sulfur-, and oxygen-comprising heterocyclic radicals comprising 4, 5 or 6, identical or different atoms, an alkoxycarbonyl radical, and alkyl radicals substituted at least at the 2-position with at least one hydroxyl radical.

8. The composition according to claim 1, wherein $R_2$ is chosen from a 2-hydroxyethyl radical, a 3-(1-pyrrolidinyl) propyl radical, a methyl radical, an acetyl radical, and hydrogen.

9. The composition according to claim 1, wherein $R_3$ is chosen from hydrogen, alkyl radicals, alkyl radicals substituted with at least one hydroxyl radical, alkyl radicals substituted with at least one amino radical, and carboxyl radicals.

10. The composition according to claim 1, wherein $R_3$ is chosen from a hydrogen atom, hydroxyl radicals, carboxyl radicals, amino radicals, hydroxymethyl radicals, and aminomethyl radicals.

11. The composition according to claim 1, wherein $R_4$ is chosen from hydrogen, alkyl radicals, alkyl radicals substituted with at least one hydroxyl radical, alkyl radicals substituted with at least one amino radical, and carboxyl radicals.

12. The composition according to claim 1, wherein $R_4$ is a hydrogen atom.

13. The composition according to claim 1, wherein the at least one oxidation base of formula (I) is chosen from:
   4-(4-Methyl-[1,4]diazepan-1-yl)phenylamine;
   4-[1,4]Diazepan-1-yl-phenylamine;
   4-[4-(3-Pyrrolidin-1-yl-propyl)-[1,4]diazepan-1-yl]phenylamine;
   2-[4-(4-Aminophenyl)-[1,4]diazepan-1-yl]ethanol;
   1-[4-(4-Aminophenyl)-[1,4]diazepan-1-yl]ethanone;
   4-(4-Aminophenyl)-[1,4]diazepane-1-carboxamidine;
   4-(4-Aminophenyl)-N,N-dimethyl-[1,4]diazepane-1-carboxamidine;
   1-(4-Aminophenyl)-4-methyl-[1,4]diazepan-6-ol;
   1-(4-Aminophenyl )-4-methyl-[1,4]diazepan-6-ylamine;
   1-(4-Aminophenyl)-4-(3-pyrrolidin-1-yl-propyl)-[1,4]diazepan-6-ol;
   1-(4-Aminophenyl)-4-(3-pyrrolidin-1-yl-propyl)-[1,4]diazepan-6-ylamine;
   1-(4-Aminophenyl)-4-(2-hydroxyethyl)-[1,4]diazepan-6-ol;
   2-[6-Amino-4-(4-aminophenyl)-[1,4]diazepan-1-yl]ethanol;
   2-[4-(4-Aminophenyl )-6-hydroxymethyl-[1,4]diazepan-1-yl]ethanol;
   2-Methyl-4-(4-methyl-[1,4]diazepan-1-yl)phenylamine;
   4-[1,4]Diazepan-1-yl-2-methylphenylamine;
   2-Methyl-4-[4-(3-pyrrolidin-1-yl-propyl)-[1,4]diazepan-1-yl]phenylamine;
   2-[4-(4-Amino-3-methylphenyl)-[1,4]diazepan-1-yl]ethanol;
   1-[4-(4-Amino-3-methylphenyl)-[1,4]diazepan-1-yl]ethanone;
   4-(4-Amino-3-methylphenyl )-[1,4]diazepane-1-carboxamidine;
   4-(4-Amino-3-methylphenyl )-N,N-dimethyl-[1,4]diazepane-1-carboxamidine;
   1-(4-Amino-3-methylphenyl)-4-methyl-[1,4]diazepan-6-ol;
   1-(4-Amino-3-methylphenyl)-4-methyl-[1,4]diazepan-6-ylamine;
   1-(4-Amino-3-methylphenyl)-4-(3-pyrrolidin-1-yl-propyl)-[1,4]diazepan-6-ol;
   1-(4-Amino-3-methylphenyl)-4-(3-pyrrolidin-1-yl-propyl)-[1,4]diazepan-6-ylamine;
   1-(4-Amino-3-methylphenyl)-4-(2-hydroxyethyl)-[1,4]diazepan-6-ol;
   2-[6-Amino-4-(4-amino-3-methylphenyl)-[1,4]diazepan-1-yl]ethanol; and
   2-[4-(4-Amino-3-methyl phenyl)-6-hydroxymethyl-[1,4]diazepan-1-yl]ethanol.

14. The composition according to claim 1, wherein the at least one oxidation base of formula (I) is present in an amount ranging from 0.001% to 10% by weight, relative to the weight of the composition.

15. The composition according to claim 14, wherein the at least one oxidation base of formula (I) is present in an amount ranging from 0.005% to 6% by weight, relative to the total weight of the composition.

16. The composition according to claim 1, further comprising at least one coupler chosen from meta-phenylenediamines, meta-aminophenols, meta-diphenols, naphthalene couplers, heterocyclic couplers and the addition salts thereof.

17. The composition according to claim 1, further comprising at least one additional oxidation base chosen from para-phenylenediamines, bisphenylalkylenediamines, para-aminophenols, ortho-aminophenols, heterocyclic bases, and the addition salts thereof.

18. The composition according to claim 1, further comprising at least one direct dye.

19. A method for the oxidation dyeing of keratin fibers comprising,
   applying to the fibers at least one dyeing composition comprising, in a medium suitable for dyeing, at least one oxidation base chosen from compounds of the following formula (I) and the addition salts thereof:

wherein:
   $R_1$ is chosen from:
      a halogen atom; and
      linear and branched $C_1$-$C_6$ hydrocarbon chains, wherein the hydrocarbon chains may be saturated or may comprise at least one bond chosen from double bonds and triple bonds, the hydrocarbon chains may form at least one ring chosen from 3- to 6-membered rings, wherein at least one carbon atom can be replaced by at least one entity chosen from oxygen, nitrogen and sulphur atoms, and an $SO_2$ group, or, when the carbon is terminal, it may be replaced by a halogen atom; provided that the radical $R_1$ does not comprise a peroxide bond, a diazo radical, a nitro radical, or a nitroso radical;
   n is a number ranging from 0 to 4 inclusive, it being understood that when n is greater than or equal to 2, then the radicals $R_1$ may be identical or different;

R₂ is chosen from:
- a hydrogen atom;
- alkyl radicals which may be unsaturated, unsubstituted and substituted with at least one radical chosen from carboxyl radicals, alkylcarbonyl radicals, alkoxycarbonyl radicals, carbamoyl radicals, mono- and dialkylcarbamoyl radicals, saturated and unsaturated, nitrogen-oxygen- and sulphur-comprising heterocyclic radicals comprising 4, 5, 6 or 7, identical or different, atoms;
- alkyl radicals which may be unsaturated, substituted at least at the 2-position by at least one radical chosen from hydroxyl radicals, alkoxy radicals, amino radicals, mono- and dialkylamino radicals, thiol radicals and halogen atoms;
- an alkylcarbonyl radical;
- an alkoxycarbonyl radical;
- a monoalkylcarbamoyl and dialkylcarbamoyl radical;
- a carbamoyl radical; and
- a radical $R_6R_7N-C=NR_5-$ wherein $R_5$, $R_6$, and $R_7$, which may be identical or different, are each chosen from hydrogen, $C_1$-$C_4$ alkyl radicals and hydroxyalkyl radicals;

R₃ is chosen from:
- a hydrogen atom;
- alkyl radicals which may be unsaturated;
- a hydroxyl radical;
- a hydroxyalkyl radical;
- an alkoxy radical;
- an alkoxyalkyl radical;
- an alkylcarbonyl radical;
- a hydroxyalkoxyalkyl radical;
- an amino radical;
- a monoalkylamino and a dialkylamino radical;
- an aminoalkyl radical, it being possible for the amine to be mono- and disubstituted with at least one identical or different radical chosen from alkyl, acetyl and hydroxyalkyl radicals;
- a hydroxy- and aminoalkyl radical;
- a carboxyl radical;
- a carboxyalkyl radical;
- a carbamoyl radical;
- a carbamoylalkyl radical;
- an alkoxycarbonyl radical; and
- a monoalkylaminocarbonyl and a dialkylaminocarbonyl radical;

R₄ is chosen from:
- alkyl radicals which may be unsaturated;
- a hydroxyalkyl radical;
- an alkoxyalkyl radical;
- an alkylcarbonyl radical;
- a hydroxyalkoxyalkyl radical;
- an aminoalkyl radical, wherein the amine may be mono- or disubstituted with at least one identical or different radical chosen from alkyl, acetyl and hydroxyalkyl radicals;
- a hydroxy- and aminoalkyl radical;
- a carboxyl radical;
- a carboxyalkyl radical;
- a carbamoyl radical;
- a carbamoylalkyl radical;
- an alkoxycarbonyl radical; and
- a monoalkylaminocarbonyl and a dialkylaminocarbonyl radical; and m is a number ranging from 0 to 4 inclusive, it being understood that when m is greater than or equal to 2, then the radicals $R_4$ may be identical or different/and developing the color with the aid of at least one oxidizing agent.

20. The method according to claim 19, wherein the at least one oxidizing agent is chosen from hydrogen peroxide, urea peroxide, alkali metal bromates, persalts, peracids and oxidase enzymes.

21. The method according to claim 19, wherein the at least one oxidizing agent is mixed at the time of use with the at least one dyeing composition.

22. The method according to claim 19, wherein the at least one oxidizing agent is applied in the form of at least one oxidizing composition simultaneously to or sequentially with the at least one dyeing composition to the fibers.

23. A multicompartment device or kit comprising,
at least one first compartment comprising at least one dyeing composition comprising, in a medium suitable for dyeing, at least one oxidation base chosen from compounds of the following formula (I) and the addition salts thereof:

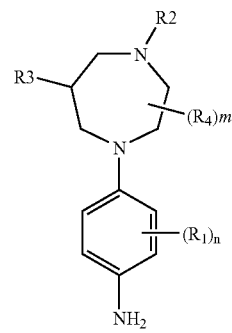

wherein:
R₁ is chosen from:
- a halogen atom; and
- linear and branched $C_1$-$C_6$ hydrocarbon chains, wherein the hydrocarbon chains may be saturated or may comprise at least one bond chosen from double bonds and triple bonds, the hydrocarbon chains may form at least one ring chosen from 3- to 6-membered rings, wherein at least one carbon atom can be replaced by at least one entity chosen from oxygen, nitrogen and sulphur atoms, and an $SO_2$ group, or, when the carbon is terminal, it may be replaced by a halogen atom; provided that the radical $R_1$ does not comprise a peroxide bond, a diazo radical, a nitro radical, or a nitroso radical;

n is a number ranging from 0 to 4 inclusive, it being understood that when n is greater than or equal to 2, then the radicals $R_1$ may be identical or different;

R₂ is chosen from:
- a hydrogen atom;
- alkyl radicals which may be unsaturated, unsubstituted and substituted with at least one radical chosen from carboxyl radicals, alkylcarbonyl radicals, alkoxycarbonyl radicals, carbamoyl radicals, mono- and dialkylcarbamoyl radicals, saturated and unsaturated, nitrogen-oxygen- and sulphur-comprising heterocyclic radicals comprising 4, 5, 6 or 7, identical or different, atoms;

alkyl radicals which may be unsaturated, substituted
at least at the 2-position by at least one radical
chosen from hydroxyl radicals, alkoxy radicals,
amino radicals, mono- and dialkylamino radicals,
thiol radicals and halogen atoms;
an alkylcarbonyl radical;
an alkoxycarbonyl radical;
a monoalkylcarbamoyl and dialkylcarbamoyl radical;
a carbamoyl radical; and
a radical $R_6R_7N\text{—}C\text{=}NR_5\text{—}$ wherein $R_5$, $R_6$, and $R_7$, which may be identical or different, are each chosen from hydrogen, $C_1$-$C_4$ alkyl radicals and hydroxyalkyl radicals;
$R_3$ is chosen from:
a hydrogen atom;
alkyl radicals which may be unsaturated;
a hydroxyl radical;
a hydroxyalkyl radical;
an alkoxy radical;
an alkoxyalkyl radical;
an alkylcarbonyl radical;
a hydroxyalkoxyalkyl radical;
an amino radical;
a monoalkylamino and a dialkylamino radical;
an aminoalkyl radical, it being possible for the amine to be mono- and disubstituted with at least one identical or different radical chosen from alkyl, acetyl and hydroxyalkyl radicals;
a hydroxy- and aminoalkyl radical;
a carboxyl radical;
a carboxyalkyl radical;
a carbamoyl radical;
a carbamoylalkyl radical;
an alkoxycarbonyl radical; and
a monoalkylaminocarbonyl and a dialkylaminocarbonyl radical;
$R_4$ is chosen from:
alkyl radicals which may be unsaturated;
a hydroxyalkyl radical;
an alkoxyalkyl radical;
an alkylcarbonyl radical;
a hydroxyalkoxyalkyl radical;
an aminoalkyl radical, wherein the amine may be mono- or disubstituted with at least one identical or different radical chosen from alkyl, acetyl and hydroxyalkyl radicals;
a hydroxy- and aminoalkyl radical;
a carboxyl radical;
a carboxyalkyl radical;
a carbamoyl radical;
a carbamoylalkyl radical;
an alkoxycarbonyl radical; and
a monoalkylaminocarbonyl and a dialkylaminocarbonyl radical; and
m is a number ranging from 0 to 4 inclusive, it being understood that when m is greater than or equal to 2, then the radicals $R_4$ may be identical or different and
at least one second compartment comprising at least one oxidizing composition.

24. A colored product obtained by oxidative condensation of at least one dyeing composition comprising:
a medium suitable for dyeing, and
at least one oxidation base comprised in said medium and chosen from compounds of the following formula (I) and the addition salts thereof:

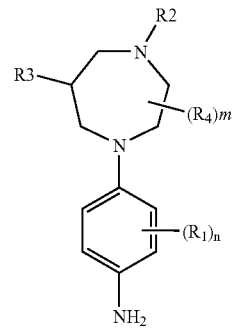

wherein:
$R_1$ is chosen from:
a halogen atom; and
linear and branched $C_1$-$C_6$ hydrocarbon chains, wherein the hydrocarbon chains may be saturated or may comprise at least one bond chosen from double bonds and triple bonds, the hydrocarbon chains may form at least one ring chosen from 3- to 6-membered rings, wherein at least one carbon atom can be replaced by at least one entity chosen from oxygen, nitrogen and sulphur atoms, and an $SO_2$ group, or, when the carbon is terminal, it may be replaced by a halogen atom; provided that the radical $R_1$ does not comprise a peroxide bond, a diazo radical, a nitro radical, or a nitroso radical;
n is a number ranging from 0 to 4 inclusive, it being understood that when n is greater than or equal to 2, then the radicals $R_1$ may be identical or different;
$R_2$ is chosen from:
a hydrogen atom;
alkyl radicals which may be unsaturated, unsubstituted and substituted with at least one radical chosen from carboxyl radicals, alkylcarbonyl radicals, alkoxycarbonyl radicals, carbamoyl radicals, mono- and dialkylcarbamoyl radicals, saturated and unsaturated, nitrogen-oxygen- and sulphur-comprising heterocyclic radicals comprising 4, 5, 6 or 7, identical or different, atoms;
alkyl radicals which may be unsaturated, substituted at least at the 2-position by at least one radical chosen from hydroxyl radicals, alkoxy radicals, amino radicals, mono- and dialkylamino radicals, thiol radicals and halogen atoms;
an alkylcarbonyl radical;
an alkoxycarbonyl radical;
a monoalkylcarbamoyl and dialkylcarbamoyl radical;
a carbamoyl radical; and
a radical $R_6R_7N\text{—}C\text{=}NR_5\text{—}$ wherein $R_5$, $R_6$, and $R_7$, which may be identical or different, are each chosen from hydrogen, $C_1$-$C_4$ alkyl radicals and hydroxyalkyl radicals;
$R_3$ is chosen from:
a hydrogen atom;
alkyl radicals which may be unsaturated;
a hydroxyl radical;
a hydroxyalkyl radical;
an alkoxy radical;
an alkoxyalkyl radical;
an alkylcarbonyl radical;

a hydroxyalkoxyalkyl radical;
an amino radical;
a monoalkylamino and a dialkylamino radical;
an aminoalkyl radical, it being possible for the amine to be mono- and disubstituted with at least one identical or different radical chosen from alkyl, acetyl and hydroxyalkyl radicals;
a hydroxy- and aminoalkyl radical;
a carboxyl radical;
a carboxyalkyl radical;
a carbamoyl radical;
a carbamoylalkyl radical;
an alkoxycarbonyl radical; and
a monoalkylaminocarbonyl and a dialkylaminocarbonyl radical;

$R_4$ is chosen from:
alkyl radicals which may be unsaturated;
a hydroxyalkyl radical;
an alkoxyalkyl radical;
an alkylcarbonyl radical;
a hydroxyalkoxyalkyl radical;
an aminoalkyl radical, wherein the amine may be mono- or disubstituted with at least one identical or different radical chosen from alkyl, acetyl and hydroxyalkyl radicals;
a hydroxy- and aminoalkyl radical;
a carboxyl radical;
a carboxyalkyl radical;
a carbamoyl radical;
a carbamoylalkyl radical;
an alkoxycarbonyl radical; and
a monoalkylaminocarbonyl and a dialkylaminocarbonyl radical; and m is a number ranging from 0 to 4 inclusive, it being understood that when m is greater than or equal to 2, then the radicals $R_4$ may be identical or different;
wherein said at least one oxidation base is present in said composition in an amount effective to dye keratin fibers.

25. A para-phenylenediamine derivative of formula (I) and the addition salts thereof:

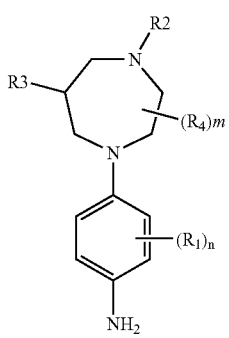

wherein:
$R_1$ is chosen from:
a halogen atom; and
linear and branched $C_1$-$C_6$ hydrocarbon chains, wherein the hydrocarbon chains may be saturated or may comprise at least one bond chosen from double bonds and triple bonds, the hydrocarbon chains may form at least one ring chosen from 3- to 6-membered rings, wherein at least one carbon atom can be replaced by at least one entity chosen from oxygen, nitrogen and sulphur atoms, and an $SO_2$ group, or, when the carbon is terminal, it may be replaced by a halogen atom; provided that the radical $R_1$ does not comprise a peroxide bond, a diazo radical, a nitro radical, or a nitroso radical;

n is a number ranging from 0 to 4 inclusive, it being understood that when n is greater than or equal to 2, then the radicals $R_1$ may be identical or different;

$R_2$ is chosen from:
a hydrogen atom;
alkyl radicals which may be unsaturated, unsubstituted and substituted with at least one radical chosen from carboxyl radicals, alkylcarbonyl radicals, alkoxycarbonyl radicals, carbamoyl radicals, mono- and dialkylcarbamoyl radicals, saturated and unsaturated, nitrogen- oxygen- and sulphur-comprising heterocyclic radicals comprising 4, 5, 6 or 7, identical or different, atoms;
alkyl radicals which may be unsaturated, substituted at least at the 2-position by at least one radical chosen from hydroxyl radicals, alkoxy radicals, amino radicals, mono- and dialkylamino radicals, thiol radicals and halogen atoms;
an alkylcarbonyl radical;
an alkoxycarbonyl radical;
a monoalkylcarbamoyl and dialkylcarbamoyl radical;
a carbamoyl radical; and
a radical $R_6R_7N$—C=$NR_5$— wherein $R_5$, $R_6$, and $R_7$, which may be identical or different, are each chosen from hydrogen, $C_1$-$C_4$ alkyl radicals and hydroxyalkyl radicals;

$R_3$ is chosen from:
a hydrogen atom;
alkyl radicals which may be unsaturated;
a hydroxyl radical;
a hydroxyalkyl radical;
an alkoxy radical;
an alkoxyalkyl radical;
an alkylcarbonyl radical;
a hydroxyalkoxyalkyl radical;
an amino radical;
a monoalkylamino and a dialkylamino radical;
an aminoalkyl radical, it being possible for the amine to be mono- and disubstituted with at least one identical or different radical chosen from alkyl, acetyl and hydroxyalkyl radicals;
a hydroxy- and aminoalkyl radical;
a carboxyl radical;
a carboxyalkyl radical;
a carbamoyl radical;
a carbamoylalkyl radical;
an alkoxycarbonyl radical; and
a monoalkylaminocarbonyl and a dialkylaminocarbonyl radical;

$R_4$ is chosen from:
alkyl radicals which may be unsaturated;
a hydroxyalkyl radical;
an alkoxyalkyl radical;
an alkylcarbonyl radical;
a hydroxyalkoxyalkyl radical;
an aminoalkyl radical, wherein the amine may be mono- or disubstituted with at least one identical or different radical chosen from alkyl, acetyl and hydroxyalkyl radicals;
a hydroxy- and aminoalkyl radical;
a carboxyl radical;
a carboxyalkyl radical;

a carbamoyl radical;
a carbamoylalkyl radical;
an alkoxycarbonyl radical; and
a monoalkylaminocarbonyl and a dialkylaminocarbonyl radical; and m is a number ranging from 0 to 4 inclusive, it being understood that when m is greater than or equal to 2, then the radicals $R_4$ may be identical or different, wherein said para-phenylenediamine derivative is not 4-(4-methyl-[1,4]diazepan-1-yl)phenylamine, 4-(4-methyl-1,4-diazacycloheptane-1-yl)aniline, 3-cyano-4-(4-t-butoxycarbonyl-1,4-cyclodiazacycloheptane) aniline, 4-(4-butoxycarbonyl-1,4-diazacycloheptane) aniline.

* * * * *

UNITED STATES PATENT AND TRADEMARK OFFICE
CERTIFICATE OF CORRECTION

PATENT NO. : 7,241,317 B2
APPLICATION NO. : 10/485855
DATED : July 10, 2007
INVENTOR(S) : Stéphane Sabelle et al.

It is certified that error appears in the above-identified patent and that said Letters Patent is hereby corrected as shown below:

In claim 1, column 27, line 50, "nitrogen-oxygen-" should read --nitrogen-, oxygen-,--.

In claim 13, column 30, lines 5-6, "2-[4-(4-Amino-3-methyl phenyl)-6-hydroxymethyl-[1,4]diazepan-1-yl]ethanol." should read --2-[4-(4-Amino-3-methylphenyl)-6-hydroxymethyl-[1,4]diazepan-1-yl]ethanol.

In claim 19, column 31, line 8, "nitrogen-oxygen-" should read --nitrogen-, oxygen-,--.

In claim 19, column 32, line 3, "different/and" should read --different; and--.

In claim 23, column 32, line 65, "nitrogen-oxygen-" should read --nitrogen-, oxygen-,--.

In claim 24, column 34, line 43, "nitrogen-oxygen-" should read --nitrogen-, oxygen-,--.

In claim 25, column 36, line 16, "nitrogen- oxygen-" should read --nitrogen-, oxygen-,--.

Signed and Sealed this

Thirteenth Day of November, 2007

JON W. DUDAS
*Director of the United States Patent and Trademark Office*